US009389216B2

(12) United States Patent
Tian et al.

(10) Patent No.: US 9,389,216 B2
(45) Date of Patent: Jul. 12, 2016

(54) METHOD FOR TESTING SETTING TIME OF CEMENT-BASED MATERIAL

(75) Inventors: Qian Tian, Nanjing (CN); Jiaping Liu, Nanjing (CN); Hang Zhang, Nanjing (CN); Yujiang Wang, Nanjing (CN); Fei Guo, Nanjing (CN); Jianye Zhang, Nanjing (CN)

(73) Assignee: SOBUTE NEW MATERIALS CO., LTD., Nanjing (CN)

( * ) Notice: Subject to any disclaimer, the term of this patent is extended or adjusted under 35 U.S.C. 154(b) by 342 days.

(21) Appl. No.: 14/131,748

(22) PCT Filed: Dec. 30, 2011

(86) PCT No.: PCT/CN2011/085011
§ 371 (c)(1),
(2), (4) Date: Jan. 9, 2014

(87) PCT Pub. No.: WO2013/097172
PCT Pub. Date: Jul. 4, 2013

(65) Prior Publication Data
US 2014/0130620 A1    May 15, 2014

(51) Int. Cl.
*G01N 33/38* (2006.01)
*G01N 11/00* (2006.01)
*G01N 13/02* (2006.01)

(52) U.S. Cl.
CPC .............. *G01N 33/383* (2013.01); *G01N 11/00* (2013.01); *G01N 2013/0208* (2013.01); *G01N 2203/0092* (2013.01)

(58) Field of Classification Search
CPC ................ G01N 33/383; G01N 11/00; G01N 2203/0092; G01N 2013/0208
See application file for complete search history.

(56) References Cited

U.S. PATENT DOCUMENTS 4,956,994 A * 9/1990 Lue ........................ G01N 3/42
73/81

4,957,556 A * 9/1990 Kunbargi ................ C04B 7/323
106/693

(Continued)

FOREIGN PATENT DOCUMENTS

CN       1821780 A     8/2006
CN     101000338 A     7/2007

(Continued)

*Primary Examiner* — Francis Gray
(74) *Attorney, Agent, or Firm* — Treasure IP Group, LLC

(57) ABSTRACT

Disclosed is a method for testing the setting time of a cement-based material: testing the capillary negative pressure of a non-bleeding cement-based material, with the time at which the capillary negative pressure reaches a threshold value A as the initial setting time, and/or the time at which the capillary negative pressure reaches a threshold value B as the final setting time, wherein threshold value A is 8-10 kPa, and threshold value B is 54-56 kPa. Alternatively, threshold value A and threshold value B are determined by the following method: formulating a cement-based material for the determination of threshold values with the same raw materials at the same formulation ratio; after vibration-compaction, placing a portion into a measuring mold; after vibration-compaction, testing the capillary negative pressure of the non-bleeding cement-based material placed in the measuring mold; under the same conditions, synchronously testing and determining the initial setting time and final setting time of the cement-based material for the determination of threshold values by a penetration resistance method; the capillary negative pressure corresponding to the initial setting time and final setting time of the cement-based material for the determination of threshold values are respectively threshold value A and threshold value B. The method can not only be used in standard tests for a laboratory cement setting time under standard temperature conditions, but can also be used to realize remote, automatic, and continuous in situ monitoring for the setting time of a cast-in-situ concrete structure.

10 Claims, 5 Drawing Sheets

(56) References Cited

U.S. PATENT DOCUMENTS

| | | | | |
|---|---|---|---|---|
| 5,095,465 A | * | 3/1992 | Stokoe, II | G01N 29/041 367/14 |
| 5,473,618 A | * | 12/1995 | Takeshita | G01R 31/30 714/733 |
| 5,741,357 A | * | 4/1998 | Sheikh | C04B 20/1088 106/692 |
| 2011/0094295 A1 | * | 4/2011 | Meadows | G01N 3/08 73/38 |
| 2011/0254573 A1 | * | 10/2011 | Shtakelberg | G01N 33/383 324/693 |

FOREIGN PATENT DOCUMENTS

| | | |
|---|---|---|
| CN | 101013125 A | 8/2007 |
| CN | 102590483 A | 7/2012 |
| RU | 2187804 C1 | 8/2002 |
| SU | 779882 A1 | 11/1980 |

\* cited by examiner (a)

(b)

▲ Is penetration resistance, ■ is pore depression

▲ Is penetration resistance,  ■ is pore depression

METHOD FOR TESTING SETTING TIME OF CEMENT-BASED MATERIAL

CROSS REFERENCE TO RELATED APPLICATION

This application claims priority to, PCT application PCT/CN2011/085011, filed on Dec. 30, 2011, entitled "Method for testing setting time of cement based material". The PCT application is incorporated herein by reference in its entirety.

TECHNICAL FIELD

The present invention relates to a method for testing setting time of cement-based materials.

BACKGROUND OF THE INVENTION

Initial setting time is a significant index for characterizing the performance and development of cast concrete. For instance, during concrete roller compaction, the allowed pouring interval of upper and lower layers of concrete shall be less than the initial setting time; the surface finishing (secondary plastering) of fresh concrete must be completed between the initial setting time and the final setting time. Therefore, it is necessary to judge the setting time of the cast concrete in construction site.

The physical significance of setting is the solidification of plastic cement grout, initial setting means the beginning of solidification which indicates the loss of fluidity of mixed materials. The following determination methods are known currently:

Penetration resistance method: this is a method capable of directly testing setting time on a laboratory or engineering basis, and also a standard method for testing setting time. It is to essentially test the development of mechanical properties of cement grout from the macroscopic perspective and deliberately set certain criterion as the basis for judging setting time. For example, in the pin-penetration test of ASTM 403 and penetration resistance instrument test of GB 8076-87, the time when the penetration resistance reaches 3.5 MPa in test (the corresponding compressive strength is about 0) is defined as the initial setting time of concrete; penetration test in both ASTM C191 and GB 1346 is used to test the setting time of cement paste. This method has long been used, but shows many problems inevitably. When testing based on this method, firstly take a small amount of fresh concrete, remove coarse aggregate above 5 mm with a vibrating screen, place the remaining mortar in a mortar cylinder and then place the cylinder on the penetration resistance instrument regularly for test. This not only causes high cost in time and effort for test operation, in particular, leads to difficulty in removal of aggregate in some stiff concrete or accelerator mixed concrete. In addition, since testing point must be changed after once test, it is hard to realize automatic collection. More importantly, with this method, it is impossible to realize in-situ monitoring of structural concrete cast in construction site, and the setting time derived from small piece test cannot truly reflect the setting time of structural concrete as the setting time of concrete is subject to temperature, namely rising temperature may quicken the setting time, the temperature of the member's concrete is always higher than that of small test piece due to heat released from cement hydration in concrete of the structure after placement and its high structural volume. Hence, it is restrictive to accurately reflect the setting time of the structural concrete by penetration resistance method.

In addition to penetration resistance method for direct testing, hydration exotherm test method is also available: traditional hydration exotherm shows the hydration dynamic properties of cement grout, and hydration reaction leading to microstructure change; generally, initial setting corresponds to certain point after transition of latent period to acceleration period. Ultrasonic pulse velocity (UPV) test method: ultrasonic wave, especially shearing wave is difficult to be transferred in concrete of plastic stage due to loose structure; with the formation of the beginning of entanglement network structure, the system gradually transforms from suspension state to coagulation state, then the time capable of transferring shearing wave corresponds to the setting time of concrete. And electrical test method: including electric conductivity and electromotive force test methods, which are used for indirect testing by relying on the test of concrete's change of electrical properties (such as electric conductivity and electromotive force) with hydration and hardening. These methods are properly sensitive, but difficult in use and operation in construction site. Related testing indexes are prone to be subject to the interference of chemical ion in concrete mixture. More importantly, testing instrument has strict requirement for ambient conditions and the testing results may be affected by the change of temperature, humidity and noise, etc. Therefore, these methods are inapplicable to the in-situ test of setting time in actual engineering structural concrete.

BRIEF SUMMARY OF THE INVENTION

According to the applicant's previous study outcomes, at standard curing temperature (20° C.±2° C.), the increase principle of penetration resistance with time is very similar to that of meniscus depression with time, namely there is a induction period and rapid increase period begins after the induction period, so a judgement method of self-desiccation shrinkage time-zero at standard curing temperature based on the meniscus depression test. This method can automatically, accurately and scientifically judges the time when self-desiccation shrinkage begins. The time-zero of self-desiccation shrinkage indicates the starting point of self-desiccation shrinkage of cement base at standard curing temperature, namely the time when acceleration period begins after induction period at 20° C.±2° C. on the development curve of meniscus depression. Although the experimental results known show similarity between the increase of meniscus depression and setting time, there is still some difference from the curve, even obvious difference in some circumstances. Upon a number of experimental researches, the applicant finally found that, if bleeding occurs on concrete surface (it is commonly seen), "time-zero" is later than setting time, thus meniscus depression begins increasing and self-desiccation shrinkage begins correspondingly after bleeding is fully absorbed back. Hence, the applicant understood that, the time-zero of self-desiccation shrinkage cannot be regarded as setting time of cement-based materials, and the results derived from known meniscus depression test can be used to judge time-zero of self-desiccation shrinkage only. Furthermore, as to engineering structure, the relation between meniscus depression and penetration resistance at standard temperature cannot be used as the basis for testing the setting time at different temperatures.

Based on a number of experimental researches, the applicant found the dominant factors affecting the difference of penetration resistance and meniscus depression, and effective measures to avoid the influences of such dominant factors. Under this precondition, the applicant put forward a method for testing setting time of cement-based materials, which can realize in-situ test of concrete's setting time. This method can be not only used for standard test of setting time of concrete in laboratory at standard temperature, but also used for in-situ monitoring of setting time of cast-in-place structural concrete remotely, automatically and continuously.

The present invention is based on:

(1) when bleeding on the concrete surface is removed in real time, the increase principle of meniscus depression at early stage inside the concrete under sealed conditions is completely the same with that of penetration resistance (see FIG. 1);

(2) within normal concrete pouring temperature range (generally 0-80° C.), under the prerequisite of the removal of bleeding and sealed maintenance, the increase of meniscus depression and penetration resistance of cement-based materials is quickened along with the temperature rise, and contrarily lowered with the decrease of temperature, but the consistency of them is completely independent of temperature (see FIG. 2).

(3) when bleeding on the surface is removed in real time, the increase principle of negative pressure of concrete capillary of mortar with coarse aggregate removed is completely consistent with that of unscreened coarse aggregate (see FIG. 3); the coarse aggregate are stones, which are commonly known in this field;

(4) the applicant conducted experimental researches and statistical analysis to meniscus depression at initial setting and final setting in sealed conditions with bleeding to be removed in real time for various concretes with different water-cement ratios, mixtures of different kinds of minerals (fly ash, siliceous dust and mineral powder), different dosages of mineral mixtures (fly ash of 0%-40%, siliceous dust of 0-10% and mineral powder of 0-70%), different types of water reducers (naphthalene series water reducer and polycarboxylate water reducer), different strength grades of cement (C25-C80) and different sand ratios (35%-55%), the test results show that, no matter how the temperature, raw materials and mix proportions change, the pore depression at initial setting is around 9 kPa, that at final setting is about 55 kPa, and when the change range of meniscus depression is ±1 kPa, the change range of testing values of corresponding setting time is less than ±5 min.

As shown in FIGS. 1 and 2, when bleeding on concrete surface is removed in real time, the development rules of penetration resistance and meniscus depression of cast & molded concrete at different temperatures are very similar, that is, the concrete shows no obvious change in the early several hours of casting and molding, and begins rapid development after a certain time point, while the initial setting time is most at the stage when meniscus depression and penetration resistance begin rising rapidly.

Moreover, with the temperature rise, the rapid development time of meniscus depression and penetration resistance may occur in advance accordingly. At different temperatures, the meniscus depression values tested at initial setting are similar (the turning point of development of meniscus depression with temperature change may vary, but the meniscus depression at initial setting changes slightly).

Therefore, the present invention is feasible technologically to avoid the impact of surface bleeding through effective measures and test meniscus depression to characterize initial setting time. Furthermore, in-situ monitoring of meniscus depression can reflect the change of setting time in actual concrete structure due to temperature change (this may be derived from hydration heat release or external ambient temperature variation), thus preventing the problem in penetration resistance test method—the testing result of the concrete taken from structure may be inconsistent with the setting time of the concrete in actual structure.

As shown in FIG. 3, when bleeding is removed, the development of meniscus depression of concrete is completely consistent with that of mortar after the removal of coarse aggregate in concrete.

The automatic, continuous and in-situ monitoring of meniscus depression of fresh concrete material in construction site is known in the prior art. See published disclosure of Patent 200610038805.0. Hence, it is possible to address the problem in testing setting time by means of penetration resistance test through the realization of remote, automatic, continuous and in-situ monitoring of setting time of concrete materials in cast structure by characterizing the initial setting time of actual cast concrete structure via remote, automatic, continuous and in-situ monitoring of meniscus depression of fresh concrete.

Based on the basic principles above, the present invention puts forward the following technical solution:

The method for testing the setting time of cement-based materials is as below: test the meniscus depression of cement-based materials without bleeding, take the time when the meniscus depression arrives at threshold A as the initial setting time and/or the time when the meniscus depression arrives at threshold B as the final setting time, wherein threshold A=9 kPa and threshold B=55 kPa; or thresholds A and B are determined by the following method: prepare the cement-based materials for the determination of the thresholds through the same mix proportions and raw materials, make the mixture compact by vibration, place some in a test mold and test the meniscus depression of cement-based materials without bleeding in the test mold after compact vibration, under the same conditions, test the initial setting time and final setting time of cement-based materials for determination of the thresholds at the same time by penetration resistance method, wherein the meniscus depressions corresponding to the initial setting time and the final setting time of cement-based materials for the determination of the thresholds are thresholds A and B respectively. The same mix proportions and raw materials indicate the same mix proportions and raw materials of cement-based materials for the determination of the thresholds and those for testing setting time.

It is feasible to test thresholds A and B at standard curing temperature, but also acceptable to perform the test above in construction site when standard curing temperature is impossible. When the setting time testing condition is unavailable, threshold A (initial setting) can be artificially set to 8-10 kPa and threshold B (final setting) is set to 54-56 kPa.

Cement-based materials are a common term in this field, which may include paste, mortar, concrete and other mixtures with cement as cementing materials or main cementing materials. The cement-based materials without bleeding can indicate either the cement-based materials themselves without bleeding, or the cement-based materials themselves with bleeding symptom but no bleeding at the bottom or bleeding on surface removed in real time. The sealed curing conditions can be those under which the cement-based materials are placed for curing (such as covering plastic film in a thickness of over 2 mm), and also those where the inside or bottom of the cement-based materials are is not in direct contact with the outside (over 150 mm from the exposure surface of concrete). When the test object is concrete structural item, to put the sensor (or probe) for testing the meniscus depression at the bottom of the concrete structure (namely the bottom of the cement-based materials above without bleeding) can avoid bleeding impact, obtain sealed ambient condition and prevent unfavourable effect on setting time testing due to water evaporation.

Preferably, lay macromolecule absorption resin cloth in a thickness of no less than 5 mm on the surface of cement-based materials, remove bleeding on the surface of cement-based materials in real time; or when the cement-based materials are concrete whose slump is no more than 220 mm, pour the cement-based materials to be tested for meniscus depression in a mold or testing mold with sealed periphery and opened upper surface, place flexible PVC plastic film in a thickness of no less than 2 mm on the upper surface of the mold or testing mold, and lead the free water bled on the concrete surface out of the mold or testing mold from the outlet on the upper surface, so as to remove bleeding on the concrete surface in real time. When the concrete slump is more than 220 mm and the concrete begins to possess self-levelling capacity, the mold with inclined upper surface is not allowed, and macromolecule absorption resin (SAP) cloth can be laid on the upper surface with a thickness of no less than 5 mm. Obviously, to remove bleeding on the surface of cement-based materials in real time, the water-absorbing efficiency of the SAP cloth above shall be no less than the total amount of bleeding. To lay macromolecule absorption resin cloth in a thickness of no less than 5 mm on the surface of the cement-based materials or flexible PVC plastic film in a thickness of no less than 2 mm on the upper surface of the mold or testing mold above can both avoid the impact of water evaporation and obtain sealed ambient condition. It is certain that the two measures above, lay macromolecule absorption resin cloth in a thickness of no less than 5 mm on the surface of the cement-based materials or flexible PVC plastic film in a thickness of no less than 2 mm on the upper surface of the mold or testing mold, can be combined in use, namely, lay macromolecule absorption resin cloth in a thickness of no less than 5 mm on the surface and then lay flexible PVC plastic film in a thickness of no less than 2 mm.

The method for testing meniscus depression is the prior art. For instance, as disclosed in CN200610038805.0, the automatic meniscus depression testing device of cement-based materials at early stage can be used to test meniscus depression, wherein the automatic meniscus depression testing device comprises a pressure sensor, a ceramic head, a gas collecting tube, a tube plug, a testing cylinder, a pin head, and a data collection and transmission device, the ceramic head is arranged at the bottom of the gas collecting tube, the tube plug is on the top, very small holes whose average diameter is 1.5-2.5 μm are on the surface and inside of the ceramic head, the pressure sensor is installed inside the testing cylinder, the pin head mounted in the front of the testing cylinder extends into the gas collecting tube after passing through the tube plug, the data obtained from the pressure sensor are analyzed and processed by the data collection and transmission device, wherein the method for testing meniscus depression includes the following steps:

a. fill the gas collecting tube with water and wet the ceramic head, the probe is formed by miniature ceramic head fully saturated, gas collecting tube and water in the gas collecting tube, and the initial pressure inside the probe is P0;

b. insert the ceramic head at the bottom of the probe into the cement-based materials, test the pressure P1 inside the probe by means of a pressure testing device, then the difference between P1 and P0 is the meniscus depression of cement-based materials.

To fully saturate the ceramic head, soak the ceramic head in gas-free water for 24 hours in advance (heat usual tap water until boiled, further heat for more than 20 min and then cool).

The gas collecting tube adopts a flexible plastic tube of a diameter of 3-5 mm so as to correspond to the diameter of the ceramic head. The connection between the ceramic head and flexible plastic tube must be compact and sealed. Before embedding it into the ceramic head, fill the flexible plastic tube with water, and insert tube plug as tightly as possible to prevent air leakage.

Preferably, the measuring range of the automatic meniscus depression testing device of cement-based materials at early stage shall be no less than 80 kPa and the accuracy shall be no lower than ±1 kPa.

The data obtained from the pressure sensor can be transferred to the remote monitoring system (such as mobile phone user) after being analyzed and processed by the data collection and transmission device. Certainly, before the data are transferred to the remote monitoring system, they shall be judged and analyzed for the arrival of setting time and then the judgment result is directly transferred. The data collection and transmission device can be one of various devices in the prior art, for example, a wireless monitoring system, or a wired monitoring system disclosed in CN200610038805.0. The data collection and transmission device includes a transmitter, an A/D converter and a computer. The data obtained from the pressure sensor are transferred from the transmitter to the A/D converter, and then sent to the computer for analysis and processing after A/D conversion.

Specifically, the present invention comprises the following operation steps (take structural concrete as an example):

1) Determination of Meniscus Depression Threshold

At standard curing temperature of laboratory (20° C.±2° C.), use raw materials and mix proportions for construction as mixture, stir the concrete in laboratory conditions, and divide the mixture into two shares, wherein one is for testing setting time as per GB 8076-87. In addition, place the remaining part in a mold with the bottom and the surrounding edges sealed airtightly, insert the ceramic probe into the interior of the concrete from the bottom horizontally, pour the concrete in the test mold and vibrate it for compaction, and then treat the upper surface of the mold and the concrete surface by the bled water removal method above according to specific conditions. When beginning test, the data collector of meniscus depression is cleared, and then the test of meniscus depression and penetration resistance is carried out simultaneously to get the meniscus depression values A and B at the initial setting and final setting, and the values A and B are input into the data collector, and set to threshold A (initial setting) and B (final setting).

It is also acceptable to perform the test above in construction site when standard curing temperature is impossible.

When the setting time testing condition is unavailable, threshold A (initial setting) can be artificially set to 9 kPa and threshold B (final setting) is set to 55 kPa.

2) Monitoring of Structural Concrete Setting Time

Before pouring concrete for construction, the ceramic probe shall be embedded in advance. The ceramic probe can be arranged in accordance with the sequence of the cast concrete surface, starting with the position where the pouring begins, then arranging 1-2 ceramic probes at the positions where the surface pouring time interval exceeds 1 h if possible. For the part with low concrete pouring depth (no more than 500 mm), the probe can be bound to the horizontal reinforcement at the bottom; as to the portion with high pouring depth, the probe can be bound to the reinforcement at the bottom via the lateral moulding board at the bottom.

After concrete pouring, clear the data collector firstly, and then set procedure in the data collector (take the remote monitoring system being a mobile phone user as an example):

a) input the constructor's phone number into the data collector as designated customer;

b) set sampling time in advance, and test meniscus depression $P_i$ at an interval of t (sampling frequency t can be set to 1 min, 2 min and 5 min . . . as desired);

c) when the in-site actual testing value $P_i$ reaches the threshold A, an automatic alarm or indication signal i1 can be automatically sent to the designated user to remind the constructor that the initial setting time of the concrete of the ith surface arrives; when the in-site actual testing value $P_i$ reaches the threshold B, an automatic alarm or indication signal i2 can be automatically sent to the designated user to remind the constructor that the final setting time of the concrete of the ith surface arrives.

The mobile phone can be set any place desired by the operator, such as in the laboratory, office and even at home, and the signal of the data collector can be transferred to GSM in a wireless manner. Therefore, the constructor can realize remote, automatic, continuous and in-situ monitoring of meniscus depression of fresh concrete in the office to characterize the initial setting time of the actually poured concrete structure, thus achieving remote, automatic, continuous and in-situ monitoring of setting time of concrete material in cast-in-place concrete structure.

DETAILED DESCRIPTION OF THE INVENTION

Figure 1:
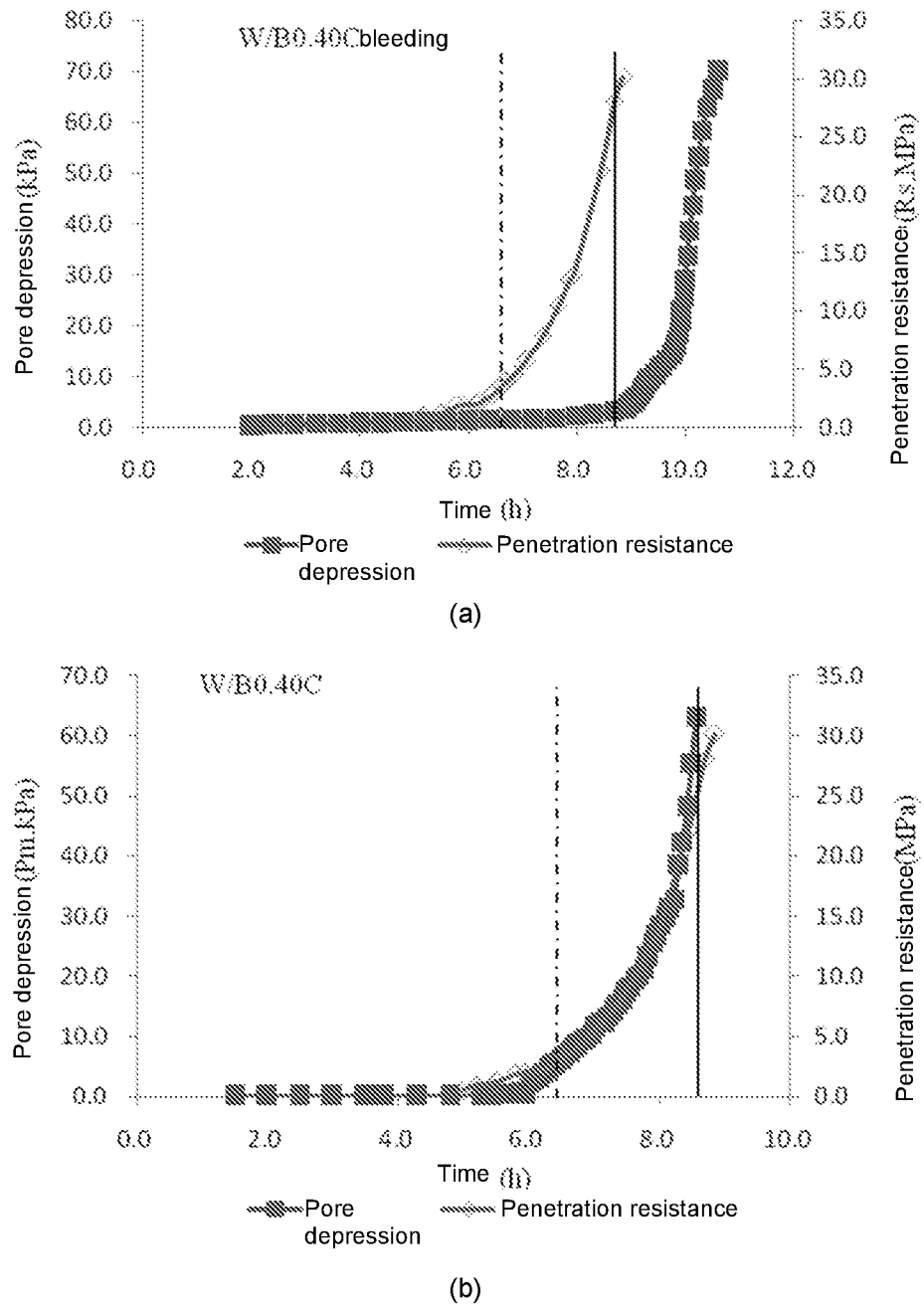
FIG. 1 shows the impact of bleeding onto the relations between the meniscus depression and the penetration resistance, wherein (a) is the case bleeding is not treated, and (b) is the case that the bled water is removed.

The test or embodiment in this section uses the automatic meniscus depression testing device of cement-based materials at early stage disclosed in CN200610038805.0, wherein the automatic meniscus depression testing device comprises a pressure sensor, a ceramic head, a gas collecting tube, a tube plug, a testing cylinder, a pin head, and a data collection and transmission device, the ceramic head is arranged at the bottom of the gas collecting tube, the tube plug is on the top, very small holes whose diameter is 2 μm are on the surface and inside of the ceramic head, the pressure sensor is installed inside the testing cylinder, the pin head mounted in the front of the testing cylinder extends into the gas collecting tube after passing through the tube plug, the data obtained from the pressure sensor are analyzed and processed by the data collection and transmission device, wherein the method for testing meniscus depression includes the following steps:

a. fill the gas collecting tube with water and wet the ceramic head, the probe is formed by miniature ceramic head fully saturated, gas collecting tube and water in the gas collecting tube, and the initial pressure inside the probe is P0;

b. insert the ceramic head at the bottom of the probe into the cement-based materials, test the pressure P1 inside the probe by means of a pressure testing device, then the difference between P1 and P0 is the meniscus depression of cement-based materials.

To fully saturate the ceramic head, soak the ceramic head in gas-free water for 24 hours in advance (heat usual tap water until boiled, further heat for more than 20 min and then cool). The gas collecting tube adopts a flexible plastic tube of a diameter of 4 mm so as to correspond to the diameter of the ceramic head. The connection between the ceramic head and flexible plastic tube must be compact and sealed. Before embedding it into the ceramic head, fill the flexible plastic tube with water, and insert tube plug as tightly as possible to prevent air leakage.

1. Investigate the Impact of Bleeding onto the Relation Between Meniscus Depression and Penetration Resistance.

Use Jinningyang 52.5R P.II cement, river sand of fineness modulus of 2.65 and broken basalt stone of 5-25 mm continuous grading. Mix proportion: 30% of mineral powder mixed with cement in mass, water-cement ratio (water/(water+mineral powder), mass percentage) of 0.40, cement-sand ratio of 2.0, sand percentage of 40%, 1.0% of total mass of JM-B naphthalene series water reducer powder mixed cementing material (cement+mineral powder) produced by Jiangsu BOTE New Materials Co., Ltd., and the setting time test refers to GB 8076-87. The bleeding rate of concrete tested per DL/T 5150-2001 is 25.5%.

(a) with bleeding not treated: at standard curing temperature of laboratory (20° C.±2° C.), use the mix proportions above to prepare concrete, and divide the mixture into two shares, wherein one is for testing setting time as per GB 8076-87. In addition, place the remaining part in a mold with the bottom and the surrounding edges sealed airtightly, insert the ceramic probe into the interior of the concrete from the bottom horizontally, and then pour the concrete in the test mold and vibrate it for compaction. When beginning test, the data collector of meniscus depression is cleared, and then the test of meniscus depression and penetration resistance is carried out simultaneously.

(b) removal of bleeding: at standard curing temperature of laboratory (20° C.±2° C.), use the mix proportions above to prepare concrete, and divide the mixture into two shares, wherein one is for testing setting time as per GB 8076-87. In addition, the place remaining part in a mold with the bottom and the surrounding edges sealed airtightly, and the upper surface opened and inclined, insert the ceramic probe into the interior of the concrete from the bottom horizontally, and then pour the concrete in the test mold and vibrate it for compaction. After molding, lay PVC plastic film in a thickness of 2 mm on the surface, and lead the free water bled on the mortar surface out of the mold or testing mold from the outlet on the upper surface, so as to remove bleeding on the mortar surface in real time. When beginning test, the data collector of meniscus depression is cleared, and then the test of meniscus depression and penetration resistance is carried out simultaneously.

The results are as shown in FIG. 1.

2. Investigate the Relations Between the Meniscus Depression and the Penetration Resistance at Different Temperatures.

At a specific temperature (20° C.±2° C.), use the mix proportions in FIG. 1 to prepare cementing mortar (Jinningyang 52.5R P.II cement, river sand of fineness modulus of 2.65, JM-B naphthalene series water reducer powder produced by Jiangsu BOTE New Materials Co., Ltd. as additives, and the bleeding rate tested per ASTM C 243 is 5.5%).

Figure 2:
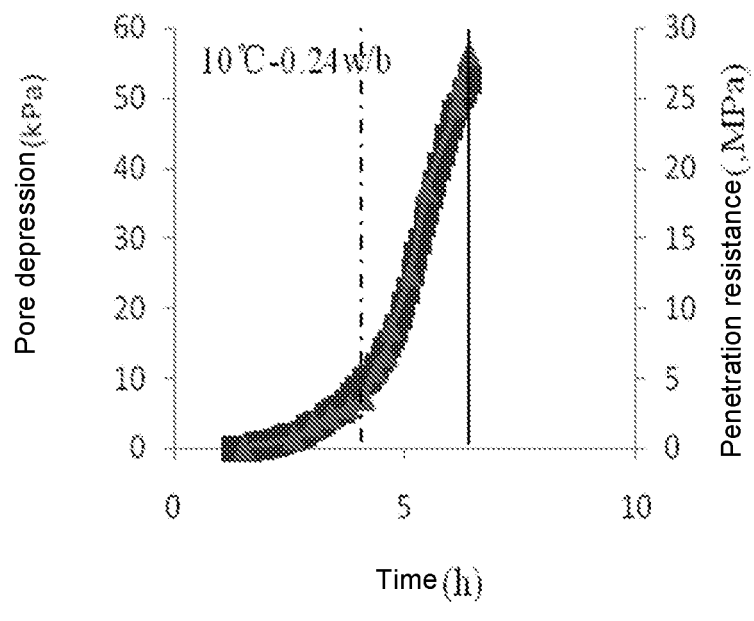
FIG. 2 shows the relations between the meniscus depression and the penetration resistance at different temperatures, wherein (a) 10° C., (b) 20° C., (c) 30° C. and (d) 40° C.
Figure 2:
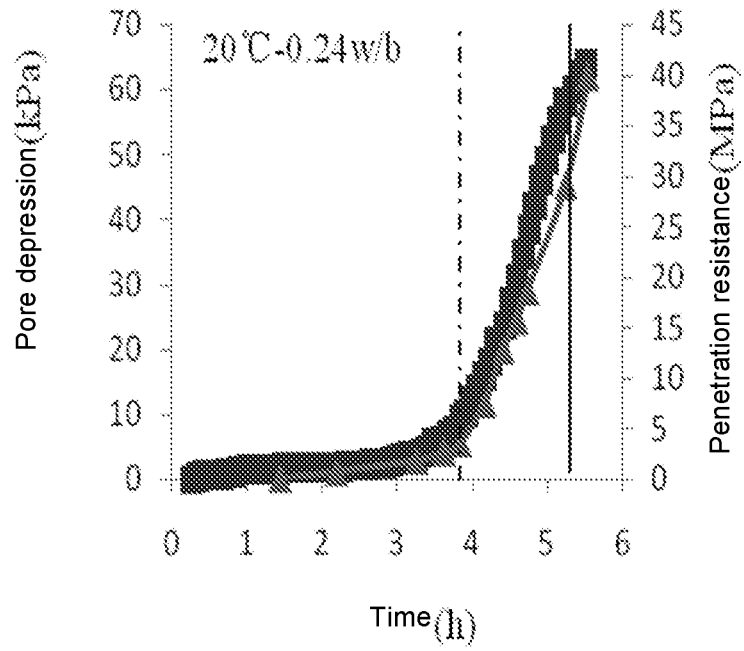
Figure 2:
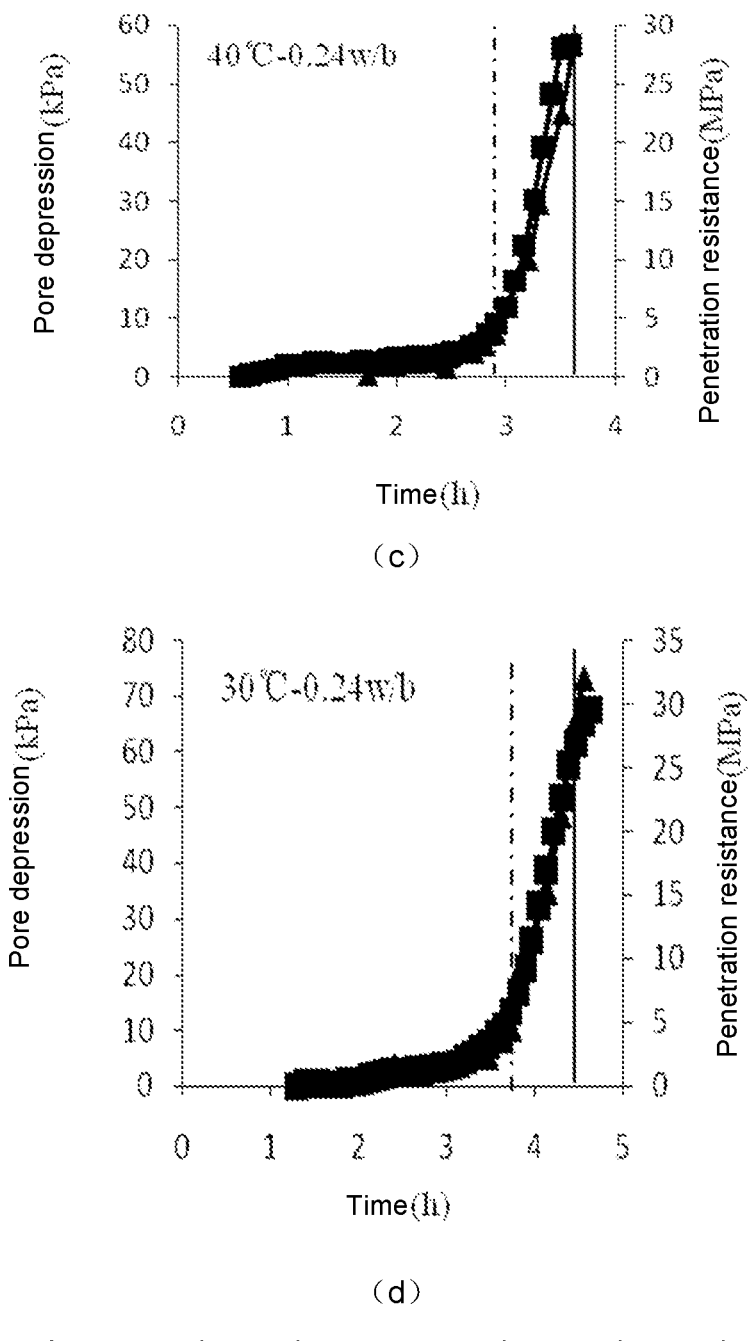

Afterwards, divide the mixture into two shares, wherein one is for testing setting time as per GB 8076-87. In addition, place the remaining part in a mold with the bottom and the surrounding edges sealed airtightly, and the upper surface inclined, insert the ceramic probe into the interior of the concrete from the bottom horizontally, and then pour the cementing mortar in the test mold and vibrate it for compaction. After molding, lay PVC plastic film in a thickness of 2 mm on the surface, and lead the free water bled on the mortar surface out of the mold or testing mold from the outlet on the upper surface, so as to remove bleeding on the mortar surface in real time. When beginning test, the data collector of meniscus depression is cleared, and then the test of meniscus depression and penetration resistance is carried out simultaneously. Four groups of the test of meniscus depression and penetration resistance are carried out simultaneously at 10° C., 20° C., 30° C. and 40° C. respectively, and the results are as shown in FIG. 2.

TABLE 1

Mix Proportions of 0.24 w/b Mortar

| Temperature | No. | Cement | Sand | Water | Additive |
|---|---|---|---|---|---|
| 10° C. | 10° C.-0.24 w/b | 5400 g | 5400 g | 1296 g | 45 g |
| 20° C. | 20° C.-0.24 w/b | 5400 g | 5400 g | 1296 g | 45 g |
| 30° C. | 30° C.-0.24 w/b | 5400 g | 5400 g | 1296 g | 45 g |
| 40° C. | 40° C.-0.24 w/b | 5400 g | 5400 g | 1296 g | 45 g |

3. Investigate the Comparison of the Meniscus Depressions of the Concrete and its Constituent Mortar.

Mix proportion: cement:water:sand:stone:additive=1:0.32:1.32:2.00:0.01; raw materials: JM-B naphthalene series water reducer powder produced by Jiangsu BOTE New Materials Co., Ltd. as additives, Jinningyang 52.5R P.II cement, river sand of fineness modulus of 2.65, broken basalt stone of 5-25 mm continuous grading. The bleeding rate of concrete tested per DL/T 5150-2001 is 6.5%.

Figure 3:
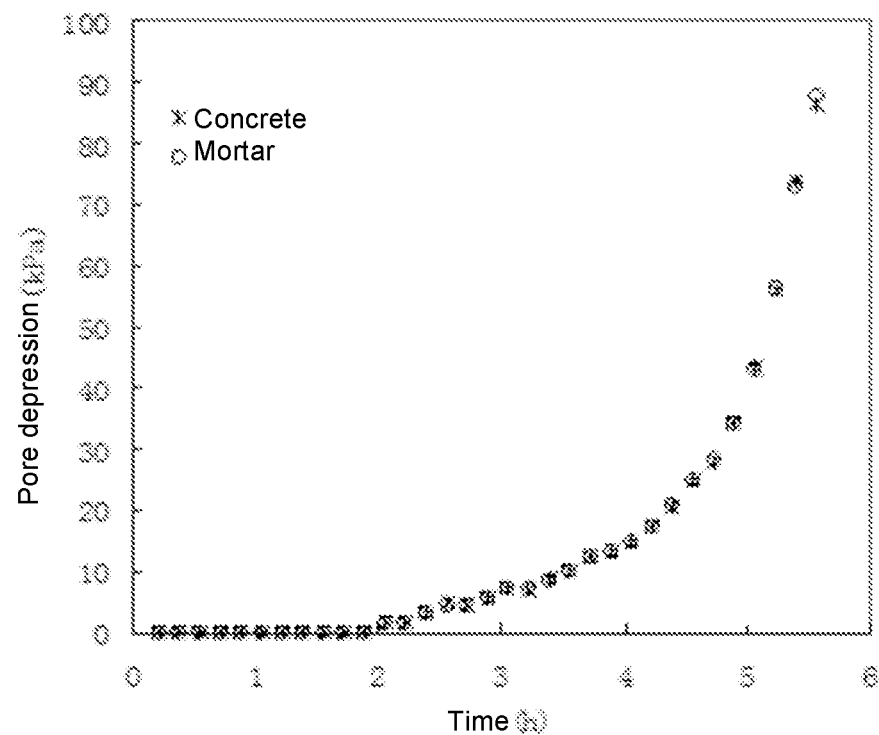
FIG. 3 is the comparison of the meniscus depressions of the concrete and its constituent mortar.

At a specific temperature (20° C.±2° C.), use the raw materials above to prepare concrete per the mix proportions, and divide the mixture into two shares, wherein one is removed for coarse aggregate above 5 mm by the method for testing setting time as per GB 8076-87. In addition, place the remaining part in a mold with the bottom and the surrounding edges sealed airtightly, and the upper surface inclined, insert the ceramic probe into the interior of the concrete from the bottom horizontally, and then pour the cementing mortar in the test mold and vibrate it for compaction. After molding, lay PVC plastic film in a thickness of 2 mm on the surface, and lead the free water bled on the mortar surface out of the mold or testing mold from the outlet on the upper surface, so as to remove bleeding on the mortar surface in real time. When beginning test, the data collector of meniscus depression is cleared, and then the test of meniscus depression is carried out simultaneously at room temperature. The results are as shown in FIG. 3.

4. Investigate the Influences of Concrete's Raw Materials and Mix Proportions to Meniscus Depression.

At a specific temperature (20° C.±2° C.), mortar is prepared by using 13 series with different water-cement ratios (0.24, 0.32 and 0.40), mixtures of different kinds of minerals (fly ash, siliceous dust and mineral powder), different dosages of mineral mixtures (fly ash of 0%-40%, siliceous dust of 0-10% and mineral powder of 0-70%) and different proportions (20%, 30% and 40% of fly ash, 5% and 10% of siliceous dust, and 30%, 50% and 70% of mineral powder), and different types of water reducers (naphthalene series water reducer and polycarboxylate water reducer); under sealed conditions with bleeding removed in real time, the relations between meniscus depression and penetration resistance are investigated in the laboratory and analyzed based on statistical data; wherein the raw materials are: Jinningyang 52.5R P.II cement, river sand of fineness modulus of 2.65, broken basalt stone of 5-25 mm continuous grading, JM-B naphthalene series water reducer powder and polycarboxylate water reducer produced by Jiangsu BOTE New Materials Co., Ltd. as additives, Grade I fly ash from Nanjing Cogeneration Power Plant, S95 finely-ground mineral powder from Jiangnan-xiaoyetian Cement and siliceous dust from Elkem.

Figure 4:
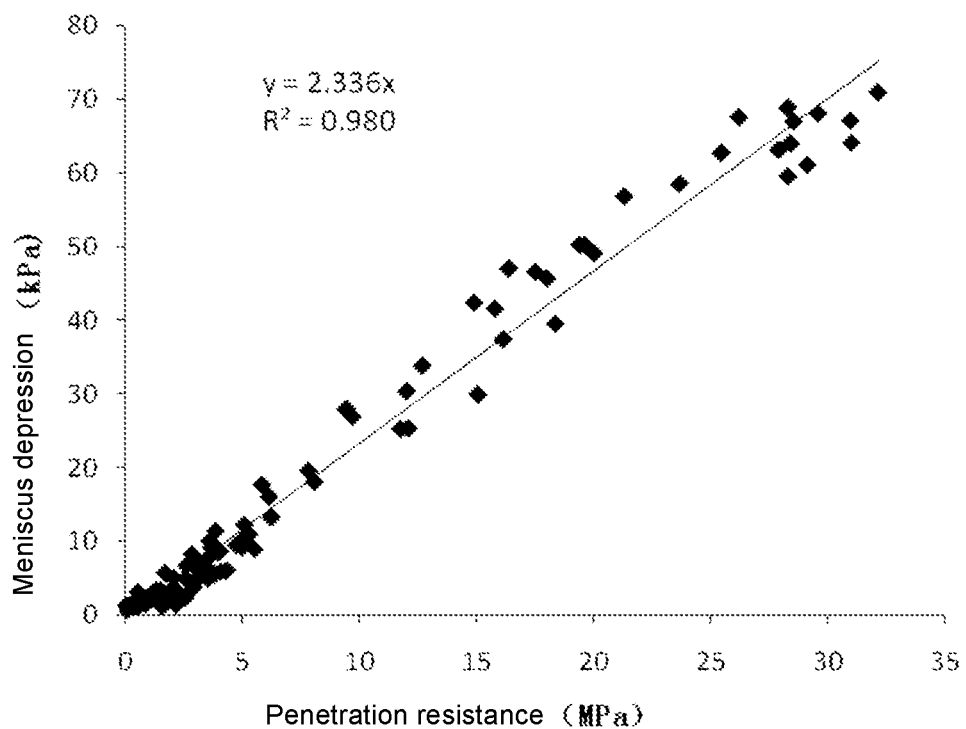
FIG. 4 shows the relations between the penetration resistance and the meniscus depression when using raw materials with different mix proportions.

Divide the mixture into two shares, wherein one is for testing setting time as per GB 8076-87. In addition, place the remaining part in a mold with the bottom and the surrounding edges sealed airtightly, and the upper surface inclined, insert the ceramic probe into the interior of the concrete from the bottom horizontally, and then pour the cementing mortar in the test mold and vibrate it for compaction. After molding, lay PVC plastic film in a thickness of 2 mm on the surface, and lead the free water bled on the mortar surface out of the mold or testing mold from the outlet on the upper surface, so as to remove bleeding on the mortar surface in real time. Begin meniscus depression test and penetration resistance test simultaneously after 1 h upon water filling. When beginning test, the data collector of meniscus depression is cleared, and the test is performed once every 5 min. After all tests, collect the 13 groups of testing results (for the convenience of display, set 5 points for each group), draw a diagram with the penetration resistance as x-coordinate and corresponding meniscus depression value as y-coordinate, as shown in FIG. 4. Make statistical analysis for all the testing results in the figure, regress the relation between meniscus depression and penetration resistance y=2.3x by means of linear fitting, and the $R^2$ regressed is 0.98. According to the result of statistical analysis in FIG. 4, as to common concrete materials, no matter how the raw materials and mix proportions change, the meniscus depression and penetration resistance measured by means of the device and method in the present invention have very consistent linear relation, so it is possible to reflect the change of penetration resistance through monitoring the variation of meniscus depression, thus further getting the setting time.

5. Relations of Change of Meniscus Depressions and that of Setting Time Tested Values During Setting Mix proportion: cement:water:sand:stone:additive=1:0.24:2.00:0.01; raw materials: JM-B naphthalene series water reducer powder produced by Jiangsu BOTE New Materials Co., Ltd. as additives, Jinningyang 52.5R P.II cement, river sand of fineness modulus of 2.65, broken basalt stone of 5-25 mm continuous grading.

At a specific temperature (20° C.±2° C.), use the raw materials above to prepare mortar per the mix proportions, and divide the mixture into two shares, wherein one is for testing setting time as per GB 8076-87. In addition, place the remaining part in a mold with the bottom and the surrounding edges sealed airtightly, and the upper surface inclined, insert the ceramic probe into the interior of the concrete from the bottom horizontally, and then pour the cementing mortar in the test mold and vibrate it for compaction. After molding, lay PVC plastic film in a thickness of 2 mm on the surface, and lead the free water bled on the mortar surface out of the mold or testing mold from the outlet on the upper surface, so as to remove bleeding on the mortar surface in real time. When beginning test, the data collector of meniscus depression is cleared, and then the test of meniscus depression is carried out simultaneously at room temperature. The results are as shown in FIG. 2.

TABLE 2

Relations Between Meniscus depression and Time Measured

| Water filling time (min) | Meniscus depression (kPa) |
|---|---|
| 78 | 0.00 |
| 83 | 0.08 |
| 88 | 0.09 |
| 93 | 0.18 |
| 98 | 0.24 |
| 103 | 0.30 |
| 108 | 0.32 |
| 113 | 0.41 |
| 118 | 0.49 |
| 123 | 0.98 |
| 128 | 1.07 |
| 133 | 1.39 |
| 138 | 1.74 |
| 143 | 2.12 |
| 148 | 2.18 |
| 153 | 2.31 |
| 158 | 2.49 |
| 163 | 2.68 |
| 168 | 2.74 |
| 173 | 2.99 |
| 178 | 3.18 |
| 183 | 3.61 |
| 188 | 3.93 |
| 193 | 4.49 |
| 198 | 5.23 |
| 203 | 6.11 |
| 208 | 7.29 |
| 213 | 8.97 |
| 218 | 10.72 |
| 223 | 13.40 |
| 228 | 16.76 |
| 233 | 21.12 |
| 238 | 26.17 |
| 243 | 32.21 |
| 248 | 38.50 |
| 253 | 45.79 |
| 258 | 51.90 |
| 263 | 57.32 |
| 268 | 61.56 |
| 273 | 65.11 |
| 278 | 67.66 |

Based on the actual measurement of penetration resistance, the initial setting time is 216 min and the final setting time is 264 min. It is obvious from the result shown in FIG. 2 that the time change is within ±5 min when the change range of meniscus depression is ±1 kPa.

Embodiment 1

See Table 3 for mix proportions in concrete construction. Raw materials: JM-III expansion agent powder produced by Jiangsu BOTE New Materials Co., Ltd. as expansion agent, JM-B naphthalene series water reducer powder as water reducer, Jinningyang 52.5R P.II cement, river sand of fineness modulus of 2.65, broken limestone of 5-31.5 mm continuous grading. The bleeding rate of concrete tested per DL/T 5150-2001 is 4.5%.

TABLE 3

Mix Proportions of Concrete Construction

| Water-cement ratio | Mix Proportions of Concrete (kg/m³) | | | | | | |
|---|---|---|---|---|---|---|---|
| | Cement | Mineral Powder | Expansion Agent | Sand | Stone | Water | Water Reducer |
| 0.32 | 328 | 140 | 52 | 733 | 1100 | 166.4 | 1.82 |

(1) Determination of Meniscus Depression Threshold

At standard curing temperature of laboratory (20° C.±2° C.), use the mix proportions shown in FIG. 2 as mixture, stir the concrete in laboratory conditions, and divide the mixture into two shares, wherein one is for testing setting time as per GB 8076-87. In addition, place the remaining part in a mold with the bottom and the surrounding edges sealed airtightly, insert the ceramic probe into the interior of the concrete from the bottom horizontally, and then pour the cementing mortar in the test mold and vibrate it for compaction. After molding, lay macromolecule absorption resin cloth in a thickness of 6 mm on the surface of the cement-based materials and then PVC plastic film in a thickness of 2 mm on the upper surface. When beginning test, the data collector of meniscus depression is cleared, and then the test of meniscus depression and penetration resistance is carried out simultaneously.

Figure 5:
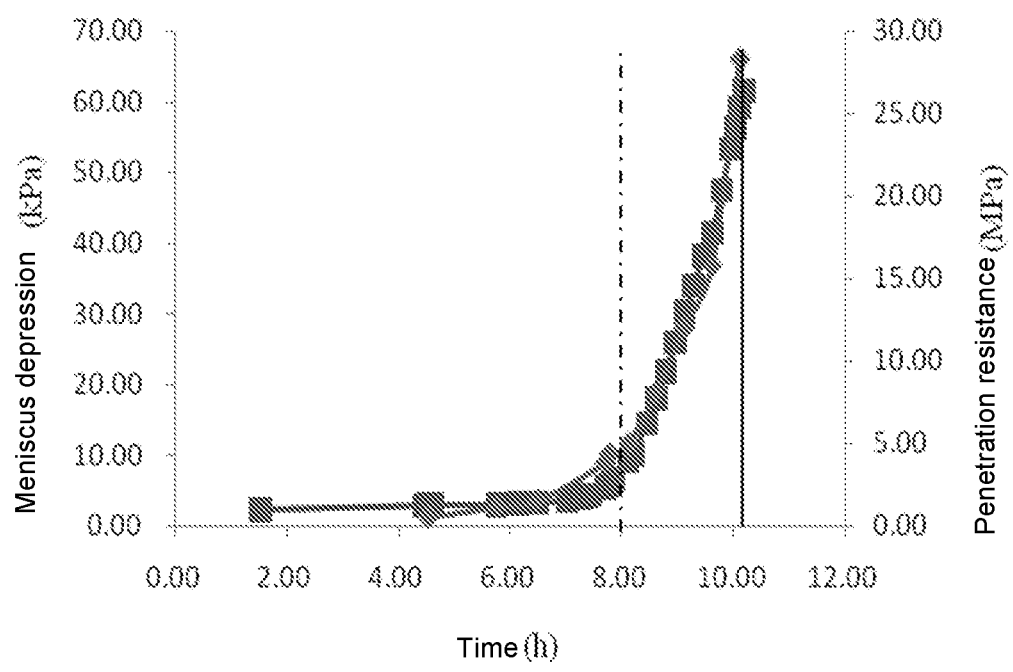
FIG. 5 is the testing result of Embodiment 1.

The relations between the meniscus depression and the penetration resistance tested in the laboratory is as shown in FIG. 5, wherein P represents meniscus depression, R represents penetration resistance, the initial setting time tested at 20° C. of the laboratory is 5.2 h, the meniscus depression at initial setting is 8.8 kPa, final setting time is 7.5 h and the meniscus depression at final setting is 54.5 kPa.

(2) Monitoring of Concrete Setting Time

The concrete pouring surface is a bearing platform of 3 m×3 m×4.5 m. Before pouring concrete, the probe is bound to the reinforcement at the bottom via the lateral moulding board at the bottom. The pressure sensor with the other end connected with the data collector is placed in construction site. The threshold A is preset to 8.8 kPa and B is set to 54.5 kPa in the meniscus depression data collector. Input the constructor's phone number into the data collector as designated customer, preset the sampling time and procedure in the data collector, and test the meniscus depression P once every 1 min. When the in-site actual testing value Pi reaches 8.8 kPa, an automatic alarm or indication signal as the initial setting time is sent to the designated user; when the in-site actual testing value P reaches 54.5 kPa, an automatic alarm or indication signal as the final setting time is sent to the designated user. The initial setting time tested in site is 4.5 h and the final setting time is 6.6 h, thus the remote, automatic, continuous and in-situ monitoring of setting time of concrete materials in concrete structure is realized.

We claim:

1. A method for testing a setting time of cement-based materials, comprising:
   testing the meniscus depression of cement-based materials without bleeding, comprising:
   taking the time when the meniscus depression arrives at threshold A as the initial setting time and/or the time when the meniscus depression arrives at threshold B as the final setting time,
   wherein threshold A=8-10 kPa and threshold B=54-56 kPa; or
   wherein thresholds A and B are determined by the following method:
   preparing the cement-based materials for the determination of the thresholds through the same mix proportions and raw materials,
   making the mixture compact by vibration, placing some in a test mold and testing the meniscus depression of cement-based materials without bleeding in the test mold after compact vibration, under the same conditions, testing the initial setting time and final setting time of cement-based materials for determination of the thresholds at the same time by penetration resistance method, wherein the meniscus depressions corresponding to the initial setting time and the final setting time of cement-based materials for the determination of the thresholds are thresholds A and B respectively.

2. The method for testing the setting time of cement-based materials as claimed in claim 1, characterized in that the cement-based materials, in sealed curing conditions and without bleeding, are either the cement-based materials themselves without bleeding on the bottom, or the cement-based materials after real time surface removal of the bleeding, and surfacing covering sealed material such as plastic films.

3. The method for testing the setting time of cement-based materials as claimed in claim 2, further comprising, laying macromolecule absorption resin cloth in a thickness of no less than 5 mm on the surface of cement-based materials, removing bleeding on the surface of cement-based materials in real time; or when the cement-based materials are concrete whose slump is no more than 220 mm, pouring the cement-based materials to be tested for meniscus depression in a mold or testing mold with sealed periphery and opened upper surface, placing flexible PVC plastic film in a thickness of no less than 2 mm on the upper surface of the mold or testing mold, and leading the free water bled on the concrete surface out of the mold or testing mold from the outlet on the upper surface, so as to remove bleeding on the concrete surface in real time.

4. The method for testing the setting time of cement-based materials as claimed in claim 3, characterized in that the meniscus depression is tested by a method, comprising:

using the automatic meniscus depression testing device of cement-based materials at early stage to test meniscus depression, wherein the device comprises a pressure sensor, a ceramic head, a gas collecting tube, a tube plug, a testing cylinder, a pin head, and a data collection and transmission device, wherein the ceramic head is arranged at the bottom of the gas collecting tube, the tube plug is on the top, very small holes whose diameter is 1.5-2.5 μm are on the surface and inside of the ceramic head, the pressure sensor is installed inside the testing cylinder, wherein the pin head mounted in the front of the testing cylinder extends into the gas collecting tube after passing through the tube plug, the data obtained from the pressure sensor are analyzed and processed by the data collection and transmission device, wherein the method for testing meniscus depression further includes the following steps:

a. filling the gas collecting tube with water and wet the ceramic head, the probe is formed by miniature ceramic head fully saturated, gas collecting tube and water in the gas collecting tube, and the initial pressure inside the probe is P0; and b. inserting the ceramic head at the bottom of the probe into the cement-based materials, test the pressure P1 inside the probe by means of a pressure testing device, then the difference between P1 and P0 is the meniscus depression of cement-based materials.

5. The method for testing the setting time of cement-based materials as claimed in claim 4, characterized in that the measuring range of the automatic meniscus depression testing device of cement-based materials at early stage shall be no less than 80 kPa and the accuracy shall be no lower than ±1 kPa.

6. The method for testing the setting time of cement-based materials as claimed in claim 1, characterized in that the cement-based materials are concrete without coarse aggregate removed and the meniscus depression of concrete without bleeding and in sealed curing conditions is directly tested.

7. The method for testing the setting time of cement-based materials as claimed in any one of claim 2, characterized in that the cement-based materials are concrete without coarse aggregate removed and the meniscus depression of concrete without bleeding and in sealed curing conditions is directly tested.

8. The method for testing the setting time of cement-based materials as claimed in any one of claim 3, characterized in that the cement-based materials are concrete without coarse aggregate removed and the meniscus depression of concrete without bleeding and in sealed curing conditions is directly tested.

9. The method for testing the setting time of cement-based materials as claimed in any one of claim 4, characterized in that the cement-based materials are concrete without coarse aggregate removed and the meniscus depression of concrete without bleeding and in sealed curing conditions is directly tested.

10. The method for testing the setting time of cement-based materials as claimed in any one of claim 5, characterized in that the cement-based materials are concrete without coarse aggregate removed and the meniscus depression of concrete without bleeding and in sealed curing conditions is directly tested.

* * * * *